United States Patent [19]

Rösner et al.

[11] Patent Number: 4,504,490
[45] Date of Patent: Mar. 12, 1985

[54] SUBSTITUTED BENZENESULFONIC ESTERS AND THEIR USE AS MEDICAMENTS FOR COMBATTING HELMINTHS

[75] Inventors: Manfred Rösner, Eppstein; Josef Urbanietz, Schwalbach; Heinz Loewe, Kelkheim; Dieter Düwel, Hofheim am Taunus; Reinhard Kirsch, Eppstein, all of Fed. Rep. of Germany

[73] Assignee: Hoechst Aktiengesellschaft, Fed. Rep. of Germany

[21] Appl. No.: 528,842

[22] Filed: Sep. 2, 1983

[30] Foreign Application Priority Data

Sep. 4, 1982 [DE] Fed. Rep. of Germany ....... 3232959

[51] Int. Cl.$^3$ .................... A61K 31/27; C07C 143/68
[52] U.S. Cl. ............................ 514/483; 260/456 A; 514/485
[58] Field of Search ................ 260/456 A; 424/300, 424/303

[56] References Cited

U.S. PATENT DOCUMENTS

| | | | |
|---|---|---|---|
| 3,996,368 | 12/1976 | Loewe et al. | 260/456 A |
| 3,996,369 | 12/1976 | Loewe et al. | 260/456 A |
| 4,176,192 | 11/1979 | Loewe et al. | 424/300 |
| 4,194,004 | 3/1980 | Niemers et al. | 424/300 |
| 4,254,143 | 3/1981 | Loewe et al. | 424/300 |

*Primary Examiner*—Nicky Chan
*Attorney, Agent, or Firm*—Finnegan, Henderson, Farabow, Garrett & Dunner

[57] ABSTRACT

New benzenesulfonic esters of the formula I

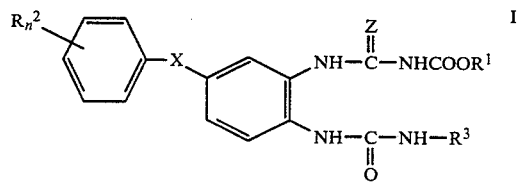

and a process for their preparation are described. The new compounds are active against helminths and can thus be used as agents to counter worms in humans and animals.

5 Claims, No Drawings

SUBSTITUTED BENZENESULFONIC ESTERS AND THEIR USE AS MEDICAMENTS FOR COMBATTING HELMINTHS

The present invention relates to new substituted Benzenesulfonic esters, a process for their preparation and the use as medicaments, in particular as anthelminthics.

Benzenesulfonic esters having anthelminthic activity are disclosed in German Offenlegungsschrift No. 2,608,238 and German Offenlegungsschrift No. 2,653,766.

New substituted benzenesulfonic esters have now been found which have anthelminthic activity and are of the formula I

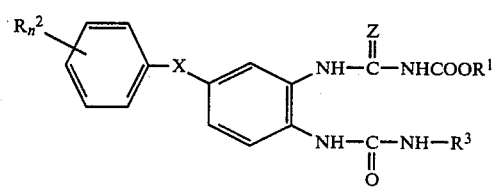

in which

R$^1$ denotes straight-chain or branched alkyl having 1–4 carbon atoms, n denotes 1, 2 or 3 and the individual substituents R$^2$, independently of one another, denote hydrogen, fluorine, chlorine, bromine, iodine, cyano, nitro, trifluoromethyl, 1,1,2,2-tetrafluoroethoxy, straight-chain or branched alkyl having 1–12 carbon atoms, cycloalkyl having 3–8 carbon atoms, alkoxy, alkylthio, alkylsulfinyl or alkylsulfonyl, each having 1–6 carbon atoms in the alkyl radical, acetyl, acetamino, or phenyl, phenoxy, phenylthio, phenylsulfinyl or phenylsulfonyl, each of which is optionally substituted once or twice by halogen, R$^3$ denotes hydrogen or —CO—R$^4$, in which R$^4$ denotes alkyl or alkoxyalkyl which are optionally substituted by halogen, and each of which have 1–6 carbon atoms in an alkyl moiety, or phenyl which is optionally substituted by halogen, methyl or methoxy, X denotes —SO$_2$—O— or —O—SO$_2$— and Z denotes =S; =N—COOR$^1$ or =NH.

Those compounds of the formula I are preferred in which

R$^1$ denotes methyl and R$^2$ denotes hydrogen, fluorine, chlorine, bromine, iodine, trifluoromethyl, 1,1,2,2-tetrafluoroethoxy, straight-chain or branched alkyl having 1–6 carbon atoms or cycloalkyl having 3–6 carbon atoms, and in which R$^3$ denotes hydrogen or —COR$^4$, in which R$^4$ denotes alkyl or alkoxyalkyl, each having 1–4 carbon atoms in an alkyl moiety, or phenyl, X denotes —SO$_2$—O— or —O—SO$_2$— and Z denotes =S or =NCOOCH$_3$ and n denotes 1 or 2.

The invention also relates to a process for the preparation of substituted benzenesulfonic esters of the formula I, which comprises reacting an aminourea derivative of the formula II

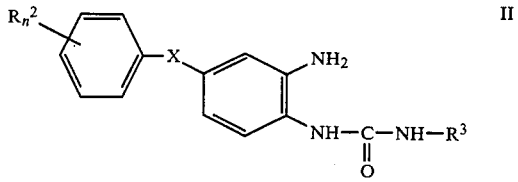

in which

R$^2$, R$^3$, X and n have the same meaning as in formula I, either (a) with an isothiocyanatocarboxylate of the formula III,

in which

R$^1$ has the abovementioned meaning, to give a compound of the formula I, in which Z represents S, or (b) with an isothioureidocarboxylate of the formula IV

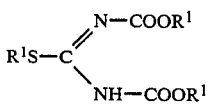

in which

R$^1$ has the abovementioned meaning, and the radicals R$^1$ which are bonded via oxygen and via sulfur can, independently of one another, be identical or different, in the presence of a solvent and an acid to give a compound of the formula I, in which Z denotes =N—COOR$^1$, (c) with an isothioureidocarboxylate of the formula IV, initially as in (b) to give a compound of the formula I, in which Z denotes =N—COOR$^1$, and then hydrolyzing this compound with a base to give a compound of the formula I, in which Z represents =NH.

The amino compounds of the general formula II are new and are obtained by reduction of nitro compounds of the formula V

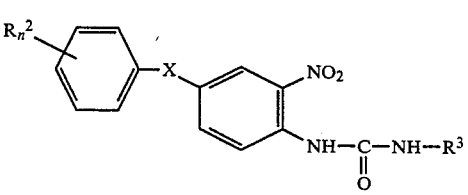

in which

R$^2$, R$^3$, X and n have the abovementioned meanings.

The nitro compounds of the formula V are likewise new and are obtained from sulfochlorides of the formula VI

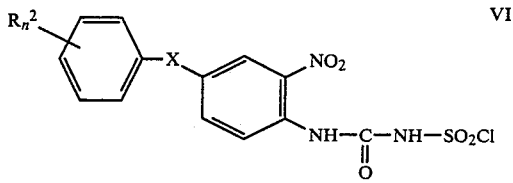

in which
R², X and n have the abovementioned meanings, by hydrolysis (V:R³=H) and, where appropriate, subsequent acylation (V:R³=—CO—R⁴).

The sulfochlorides of the formula VI are likewise new and are obtained from nitroamino compounds of the general formula VII

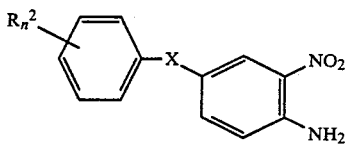

in which
R², X and n have the abovementioned meanings, by reaction with N-chlorosulfonyl isocyanate VIII

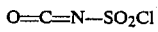=C=N—SO₂Cl    

Nitroamines of the formula VII are known from German Offenlegungsschrift No. 2,441,201 and German Offenlegungsschrift No: 2,441,202 (corresponding to U.S. Pat. No. 3,996,368 and U.S. Pat. No. 3,996,369) and are prepared by the methods given there or by analogous routes.

When X in formula VII denotes —SO₂—O—, the preparation is advantageously carried out by reaction of an optionally R²ₙ-substituted benzenesulfonyl chloride with 4-amino-3-nitrophenol or its salt in an inert solvent such as acetone, in the presence of an organic or inorganic base, such as triethylamine or sodium hydroxide.

When X in formula VII denotes —O—SO₂—, the preparation is advantageously carried out by reaction of an optionally R²ₙ-substituted phenol with 4-chloro-3-nitrobenzenesulfonyl chloride in an inert solvent such as acetone, in the presence of an organic or inorganic base, such as triethylamine or sodium hydroxide and subsequent chlorine exchange in an inert solvent, such as dioxane, with gaseous ammonia at elevated temperature, advantageously at 100°-140° C. and under elevated pressure.

The reaction of the nitroamines of the formula VII with N-chlorosulfonyl isocyanate VIII takes place in an aprotic solvent at −20° to +50° C., preferably between 0° and 20° C. Examples of suitable solvents are hydrocarbons, such as hexane, cyclohexane, benzene, toluene or xylene, ethers, such as diisopropyl ether, dioxane or dimethoxyethane, or chlorinated hydrocarbons, such as methylene chloride, chloroform, carbon tetrachloride, 1,2-dichloroethane or chlorobenzene, and acetonitrile.

In a preferred embodiment, a slight excess (10–20%) of VIII in toluene is employed at about 10° C.

The hydrolysis of the sulfochlorides VI takes place by stirring with water or an aqueous solution of an inorganic or organic acid, such as hydrochloric acid, sulfuric acid, phosphoric acid, nitric acid, formic acid, acetic acid, trifluoroacetic acid or p-toluenesulfonic acid, optionally with the addition of a solvent, such as methanol, ethanol or acetone, at −20° to +100° C. The reaction is preferably carried out at 0° to 80° C. in 1-2N HCl. The sulfonic acid initially formed on hydrolysis is unstable and decomposes into SO₃ and a nitro compound V with R³=H. A compound V with R³=—CO—R⁴ can be optionally prepared from this by reaction with an acid anhydride (R⁴—CO)₂O, advantageously in an inert solvent, such as toluene, methylene chloride or acetonitrile, at −20° to +50° C., in the presence of a catalytic amount of a strong inorganic or organic acid, such as concentrated sulfuric acid, methanesulfonic acid or trifluoroacetic acid. In a preferred embodiment, an excess of the acid anhydride is used at 0°-40° C. and concentrated sulfuric acid is used as the catalyst.

The nitro compounds of the formula V are hydrogenated to give the amino compounds of the formula II by reduction, for example with Raney nickel, in a solvent, for example methanol or dimethylformamide, under normal pressure or in an autoclave under pressure.

In process variant (a), the reaction of the amino compounds II with an isothiocyanatocarboxylate III is carried out with or without the addition of a solvent at −20° to +140° C. Examples of suitable solvents are: diisopropyl ether, tetrahydrofuran, dioxane, dimethoxyethane, ethyl acetate, acetone, butanone, toluene, xylene, chlorobenzene, methylene chloride, chloroform, carbon tetrachloride, 1,2-dichloroethane, methanol, ethanol, isopropanol or 2-methoxyethanol. The reaction is preferably carried out with an equimolar amount or a slight excess (10–20%) of the isothiocyanatocarboxylate at 20°-50° C. in dioxane or ethyl acetate.

In process variant (b), the reaction of the amino compounds II with an isothioureidocarboxylate IV is carried out in the presence of a solvent and an acid at 0°-120° C. Suitable solvents are, in particular, polar solvents, such as, for example, water, methanol, ethanol, isopropanol, butanol or 2-methoxyethanol, but also, for example, ethyl acetate, dioxane, toluene, chloroform or mixtures thereof. Acids which can be used are inorganic or organic acids, such as hydrochloric acid, sulfuric acid, nitric acid, phosphoric acid, formic acid, acetic acid, propionic acid and p-toluenesulfonic acid. The reaction is preferably carried out in methanol, alone or mixed with ethyl acetate, with the addition of glacial acetic acid or p-toluenesulfonic acid at the reflux temperature of the mixture used.

In process variant (c), those compounds of the general formula I which have been prepared by process variant (b) (Z denotes =NCOOR¹) are hydrolyzed and decarboxylated, with inorganic or organic bases, to give compounds of the formula I
in which
Z denotes =NH.

Examples of suitable bases are ammonia, alkali metal or alkaline earth metal carbonates and hydroxides, such as potassium or barium carbonate, sodium or potassium hydroxide or amines, such as methylamine, ethylamine, butylamine, diethylamine, diisopropylamine, triethylamine or ethyl diisopropylamine, in a solvent, such as water, methanol, ethanol, isopropanol, ethyl acetate, acetone, dioxane, toluene or mixtures of these. The temperature used for this reaction can be between 0° and 120° C. For example, butylamine is used in methanol, advantageously at the boiling point of the reaction mixture.

Those compounds of the formula I
in which
Z denotes =NCOOR$^1$ or =NH,
process variants (b) and (c), can exist in tautomeric forms

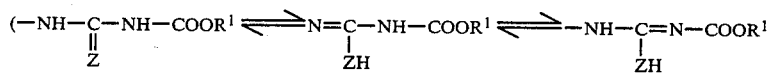

in formula I). Therefore the general formula I also comprises all tautomers and their mixtures.

Examples of compounds according to the invention
of the formula I
in which
X denotes —SO$_2$—O— are as follows

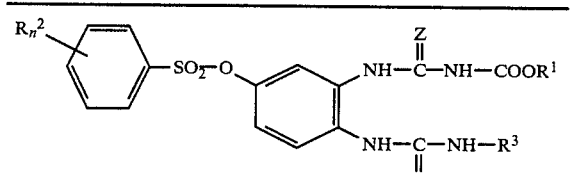

| $R_n^2$ | $R^3$ | $R^1$ | Z |
|---|---|---|---|
| 4-C$_6$H$_{11}$ | H | CH$_3$ | N—COOCH$_3$ |
| 4-C$_6$H$_{11}$ | H | CH$_3$ | NH |
| 4-C$_6$H$_{11}$ | H | CH$_3$ | S |
| 4-C$_6$H$_{11}$ | CH$_3$CO | CH$_3$ | N—COOCH$_3$ |
| 4-C$_6$H$_{11}$ | CH$_3$CO | CH$_3$ | S |
| H | CH$_3$CO | CH$_3$ | N—COOCH$_3$ |
| H | CH$_3$CO | CH$_3$ | S |
| 2-CF$_3$ | CH$_3$CO | CH$_3$ | N—COOCH$_3$ |
| 2-CF$_3$ | CH$_3$CO | CH$_3$ | S |
| 3-CF$_3$ | H | C$_2$H$_5$ | N—COOC$_2$H$_5$ |
| 3-CF$_3$ | H | iC$_3$H$_7$ | N—COOiC$_3$H$_7$ |
| 3-CF$_3$ | C$_6$H$_5$CO | CH$_3$ | N—COOCH$_3$ |
| 3-CF$_3$ | H | CH$_3$ | NH |
| 3-CF$_3$ | CH$_3$OCH$_2$CO | CH$_3$ | N—COOCH$_3$ |
| 3-CF$_3$ | CH$_3$OCH$_2$CO | CH$_3$ | S |
| 4-CF$_3$ | H | CH$_3$ | N—COOCH$_3$ |
| 4-CF$_3$ | H | CH$_3$ | NH |
| 4-CF$_3$ | H | CH$_3$ | S |
| 4-CF$_3$ | CH$_3$CO | CH$_3$ | N—COOCH$_3$ |
| 4-CF$_3$ | CH$_3$CO | CH$_3$ | S |
| 3,5-(CF$_3$)$_2$ | CH$_3$CO | CH$_3$ | N—COOCH$_3$ |
| 3,5-(CF$_3$)$_2$ | CH$_3$CO | CH$_3$ | NH |
| 3-CHF$_2$CF$_2$O | H | CH$_3$ | NH |
| 3-CHF$_2$CF$_2$O | CH$_3$CO | CH$_3$ | N—COOCH$_3$ |
| 3-CHF$_2$CF$_2$O | CH$_3$CO | CH$_3$ | S |
| 3-CHF$_2$CF$_2$O | H | iC$_3$H$_7$ | S |
| 4-F | H | CH$_3$ | NH |
| 4-F | CH$_3$CO | CH$_3$ | N—COOCH$_3$ |
| 4-F | CH$_3$CO | CH$_3$ | S |
| 4-F | CH$_3$OCH$_2$CO | CH$_3$ | N—COOCH$_3$ |
| 4-F | CH$_3$OCH$_2$CO | CH$_3$ | S |
| 4-Br | CH$_3$CO | CH$_3$ | N—COOCH$_3$ |
| 4-Br | CH$_3$CO | CH$_3$ | S |
| 2,5-Cl$_2$ | CH$_3$CO | CH$_3$ | N—COOCH$_3$ |
| 2,5-Cl$_2$ | CH$_3$CO | CH$_3$ | S |
| 2,4-Cl$_2$ | H | CH$_3$ | N—COOCH$_3$ |
| 2,4-Cl$_2$ | H | CH$_3$ | S |
| 3-Br, 4-F | H | CH$_3$ | N—COOCH$_3$ |
| 3-Br, 4-F | H | CH$_3$ | S |
| 3,4-F$_2$ | H | CH$_3$ | N—COOCH$_3$ |
| 3,4-F$_2$ | H | CH$_3$ | NH |
| 3,4-F$_2$ | H | CH$_3$ | S |
| 3,4-F$_2$ | H | C$_4$H$_9$ | S |
| 3,4-Br$_2$ | H | CH$_3$ | N—COOCH$_3$ |
| 3,4-Br$_2$ | H | CH$_3$ | S |
| 2-Cl, 4-Br | H | CH$_3$ | N—COOCH$_3$ |
| 2-Cl, 4-Br | H | CH$_3$ | S |
| 2-Cl | H | CH$_3$ | N—COOCH$_3$ |
| 2-Cl | H | CH$_3$ | S |
| 2-Br | H | CH$_3$ | N—COOCH$_3$ |
| 2-Br | H | CH$_3$ | S |
| 2-F | H | CH$_3$ | N—COOCH$_3$ |
| 2-F | H | CH$_3$ | S |
| 4-I | H | CH$_3$ | N—COOCH$_3$ |
| 4-I | H | CH$_3$ | NH |
| 4-I | H | CH$_3$ | S |
| 3-F | H | CH$_3$ | N—COOCH$_3$ |
| 3-F | H | CH$_3$ | S |
| 4-CH$_3$O | CH$_3$CO | CH$_3$ | N—COOCH$_3$ |
| 4-CH$_3$O | CH$_3$CO | CH$_3$ | S |
| 4-CH$_3$S | H | CH$_3$ | N—COOCH$_3$ |
| 4-CH$_3$S | H | CH$_3$ | S |
| 4-CH$_3$SO | H | CH$_3$ | N—COOCH$_3$ |
| 4-CH$_3$SO | H | CH$_3$ | S |
| 4-CH$_3$SO$_2$ | H | CH$_3$ | N—COOCH$_3$ |
| 4-CH$_3$SO$_2$ | H | CH$_3$ | S |
| 3-CH$_3$SO$_2$ | H | CH$_3$ | N—COOCH$_3$ |
| 3-CH$_3$SO$_2$ | H | CH$_3$ | NH |
| 3-CH$_3$SO$_2$ | H | CH$_3$ | S |
| 4-C$_6$H$_5$O | H | CH$_3$ | N—COOCH$_3$ |
| 4-C$_6$H$_5$O | H | CH$_3$ | S |
| 4-C$_6$H$_5$S | H | CH$_3$ | N—COOCH$_3$ |
| 4-C$_6$H$_5$S | H | CH$_3$ | NH |
| 4-C$_6$H$_5$S | H | CH$_3$ | S |
| 4-C$_6$H$_5$SO | H | CH$_3$ | N—COOCH$_3$ |
| 4-C$_6$H$_5$SO | H | CH$_3$ | S |
| 4-C$_6$H$_5$SO$_2$ | H | CH$_3$ | N—COOCH$_3$ |
| 4-C$_6$H$_5$SO$_2$ | H | CH$_3$ | S |
| 4-C$_6$H$_5$CH$_2$ | H | CH$_3$ | N—COOCH$_3$ |
| 4-C$_6$H$_5$CH$_2$ | H | CH$_3$ | S |
| 2,3-Cl$_2$ | H | CH$_3$ | N—COOCH$_3$ |
| 2,3-Cl$_2$ | H | CH$_3$ | S |
| 3-CN | H | CH$_3$ | N—COOCH$_3$ |
| 3-CN | H | CH$_3$ | S |
| 3-NO$_2$ | H | CH$_3$ | N—COOCH$_3$ |
| 3-NO$_2$ | H | CH$_3$ | S |
| 4-F—C$_6$H$_4$ | H | CH$_3$ | N—COOCH$_3$ |
| 4-F—C$_6$H$_4$ | H | CH$_3$ | S |
| 4-Cl—C$_6$H$_4$ | H | CH$_3$ | N—COOCH$_3$ |
| 4-Cl—C$_6$H$_4$ | H | CH$_3$ | S |
| 4-Br—C$_6$H$_4$ | H | CH$_3$ | N—COOCH$_3$ |
| 4-Br—C$_6$H$_4$ | H | CH$_3$ | S |

Examples of compounds of the formula I according to the invention
in which
X denotes —O—SO$_2$—
are as follows

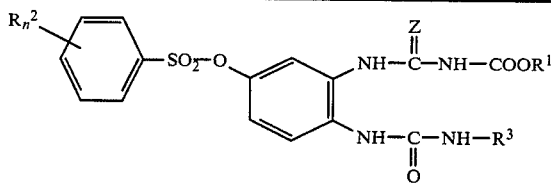

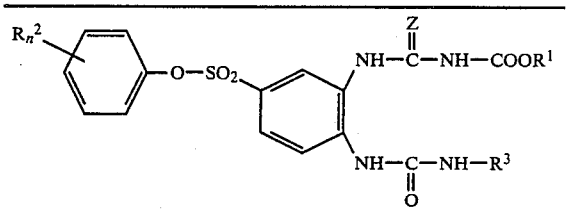

| $R_n^2$ | $R^3$ | $R^1$ | Z |
| --- | --- | --- | --- |
| H | H | CH₃ | NH |
| H | H | C₂H₅ | N—COOC₂H₅ |
| H | H | C₃H₇ | N—COOC₃H₇ |
| H | H | C₄H₉ | N—COOC₄H₉ |
| H | C₂H₅CO | CH₃ | S |
| H | C₂H₅CO | C₂H₅ | S |
| H | C₂H₅CO | iC₃H₇ | S |
| H | CH₃OCH₂CO | CH₃ | N—COOCH₃ |
| H | CH₃OCH₂CO | CH₃ | S |
| H | C₆H₅CO | CH₃ | S |
| 4-C₂H₅ | CH₃CO | CH₃ | N—COOCH₃ |
| 4-sec.C₄H₉ | CH₃CO | CH₃ | N—COOCH₃ |
| 2,3-Cl₂ | H | CH₃ | N—COOCH₃ |
| 4-Cl | H | CH₃ | N—COOCH₃ |
| 4-Cl | H | CH₃ | NH |
| 4-Cl | H | CH₃ | S |
| 4-Br | H | CH₃ | N—COOCH₃ |
| 4-Br | H | CH₃ | S |
| 4-I | H | CH₃ | N—COOCH₃ |
| 4-I | H | CH₃ | S |
| 4-C₆H₅ | H | CH₃ | N—COOCH₃ |
| 3,4-Cl₂ | H | CH₃ | N—COOCH₃ |
| 3,4-Cl₂ | H | CH₃ | S |
| 3-CF₃ | C₃H₇CO | CH₃ | N—COOCH₃ |
| 3-CF₃ | C₃H₇CO | CH₃ | S |
| 3-CF₃ | C₃H₇CO | C₂H₅ | S |
| 3-CF₃ | CH₃OCH₂CO | CH₃ | N—COOCH₃ |
| 3-CF₃ | CH₃OCH₂CO | CH₃ | NH |
| 3-CF₃ | CH₃OCH₂CO | CH₃ | S |
| 3-CN | H | CH₃ | N—COOCH₃ |
| 3-CN | H | CH₃ | S |
| 4-CN | H | CH₃ | N—COOCH₃ |
| 4-CN | H | CH₃ | S |
| 3-OCH₃ | H | CH₃ | N—COOCH₃ |
| 3-OCH₃ | H | CH₃ | S |
| 4-OCH₃ | H | CH₃ | N—COOCH₃ |
| 4-OCH₃ | H | CH₃ | S |
| 3,4-(OCH₃)₂ | H | CH₃ | N—COOCH₃ |
| 3,4-(OCH₃)₂ | H | CH₃ | S |
| 3-NO₂ | H | CH₃ | S |
| 4-(CH₃CONH) | H | CH₃ | S |
| 4-C₆H₅CH₂ | H | CH₃ | N—COOCH₃ |
| 4-C₆H₅CH₂ | H | CH₃ | S |
| 4-C₆H₅O | H | CH₃ | N—COOCH₃ |
| 4-C₆H₅O | H | CH₃ | S |
| 4-C₆H₅S | H | CH₃ | N—COOCH₃ |
| 4-C₆H₅S | H | CH₃ | S |
| 4-C₆H₅SO | H | CH₃ | S |
| 4-C₆H₅SO₂ | H | CH₃ | S |

The new substituted benzenesulfonic esters of the formula I according to the invention are valuable chemotherapeutic agents and are suitable for controlling parasitic diseases of humans and animals.

They are particularly effective against a large number of helminths, for example Haemonchus, Trichostrongylus, Ostertagia, Cooperia, Chabertia, Strongyloides, Oesophagostomum, Hyostrongylus, Ancylostoma, Ascaris and Heterakis as well as Fasciola. The efficacy against gastrointestinal strongylidae, lung worms and liver flukes by which, in particular, domestic and useful animals are affected. For this reason, the compounds according to the invention will be particularly used in verterinary medicaments.

The compounds of the formula I will be administered, depending on the status of the case, in doses between 0.1 and 50 mg per kg of body weight for 1 to 14 days.

Suitable for oral administration are tablets, coated tablets, capsules, boli, powders, granules or pastes, which contain the active compounds together with customary auxiliaries or vehicles, such as starch, cellulose powder, talc, magnesium stearate, sugar, gelatin, calcium carbonate, finely divided silica, carboxymethylcellulose or similar materials.

The products of the process not only have excellent efficacy on oral administration, they can also be administered parenterally. Solutions are suitable for parenteral administration, for example oily solutions which are prepared using sesame oil, olive oil or synthetic triglycerides, optionally with an additive, such as, for example, tocopherol as an antioxidant, and/or the use of surface-active materials, such as sorbitan fatty acid esters. Aqueous suspensions are also suitable, these being prepared using ethoxylated sorbitan fatty acid esters, and/or with the addition of thickening agents, such as polyethylene glycol or carboxymethylcellulose.

The concentrations of the active compounds according to the invention in the products prepared from them are preferably between 0.5 and 25 percent by weight for use as veterinary medicaments; the concentrations of the active compounds are preferably between 20 and 80 percent by weight for use as human medicaments.

The new aminourea derivatives of the formula II and the new nitro compounds of the formula V likewise have anthelminthic efficacy. In addition, they can be used, as can the new sulfochlorides of the formula VI, as intermediates for the preparation of anthelminthics as described above.

EXAMPLE 1

Process (a)

1-Methoxycarbonyl-3-(5-phenoxysulfonyl-2-ureidophenyl)-thiourea (formula I)

25 ml of methoxycarbonyl isothiocyanate are added dropwise to 23.5 g of 5-phenoxysulfonyl-2-ureidoaniline in 100 ml of dioxane, with stirring, the temperature rising to about 35° C. The mixture is stirred for a further four hours without cooling, the dioxane is distilled off, the residue is stirred with diisopropyl ether and the solid is filtered off with suction.

After crystallization from methanol, melting point 190° C., decomposition.

EXAMPLE 2

(Process (b))

N,N'-Bismethoxycarbonyl-N''-(5-phenoxysulfonyl-2-ureidophenyl)guanidine (formula I)

15.3 g of 5-phenoxysulfonyl-2-ureidoaniline, 12 g of N,N'-bismethoxycarbonyl-S-methylisothiourea and 100 mg of p-toluenesulfonic acid in 80 ml of methanol and 80 ml of ethyl acetate are stirred under reflux for four hours. After cooling down, the solid is filtered off with suction and washed with ethyl acetate and diisopropyl ether. For recrystallization, the solid is dissolved in dimethylformamide at about 50° C., treated with active charcoal, filtered, ethyl acetate and diisopropyl ether are added and crystallization is allowed to occur, melting point 193° C., decomposition.

EXAMPLE 3

(Process (a))

1-[2-(3-acetylureido)-5-phenoxysulfonylphenyl]-3-methoxycarbonylthiourea (formula I)

17.5 g of 2-(3-acetylureido)-5-phenoxysulfonylaniline and 15 ml of methoxycarbonyl isothiocyanate in 150 ml of dioxane are heated at 80° C. for 5 minutes, and then stirring is continued without heating. After slowly cooling down to room temperature, the dioxane is distilled out under reduced pressure. The residue is dissolved in dimethylformamide, the solution is treated with active charcoal and evaporated and then methanol is added. After cooling down, the precipitate is filtered off with suction and washed with methanol and diisopropyl ether. Melting point 215° C., decomposition.

EXAMPLE 4

5-Phenoxysulfonyl-2-ureidoaniline (formula II)

33.7 g of 5-phenoxysulfonyl-2-ureidonitrobenzene in 250 ml of methanol and 250 ml of 2-methoxyethanol are hydrogenated under normal pressure with a catalytic amount of Raney nickel. After uptake of hydrogen is complete, the catalyst is filtered off with suction, washed with dimethylformamide and the solution is evaporated under reduced pressure, induced to crystallize with methanol, and the crystals are filtered off with suction and washed with methanol, melting point 180° C., decomposition.

EXAMPLE 5

5-Phenoxysulfonyl-2-ureidonitrobenzene (formula V)

30 ml of N-chlorosulfonyl isocyanate dissolved in 70 ml of toluene are rapidly added dropwise, at +10° C., to 88.2 g of 2-amino-5-phenoxysulfonylnitrobenzene in 750 ml of toluene. The mixture is stirred for a further hour while cooling, and the precipitate is filtered off with suction, washed with diisopropyl ether and dried in a desiccator over potassium hydroxide. 88 g of the 2-(3-chlorosulfonylureido)-5-phenoxysulfonylnitrobenzene produced are introduced, with stirring and cooling, into 800 ml of 1N HCl. After 30 minutes, the clear solution is briefly warmed to 80° C. (precipitation) and then left to stand. After cooling down, the solid is filtered off with suction and washed with water to neutrality, melting point 190° C.

EXAMPLE 6

2-(3-Acetylureido)-5-phenoxysulfonylnitrobenzene (formula V)

1 ml of concentrated sulfuric acid is added, with stirring, to 50.5 g of 5-phenoxysulfonyl-2-ureidonitrobenzene in 250 ml of acetic anhydride. A clear solution is produced, followed rapidly by precipitation. The mixture is stirred for a further two hours, and the solid is filtered off with suction and washed consecutively with glacial acetic acid and diisopropyl ether, melting point 198° C., decomposition.

EXAMPLE 7

2-(3-Acetylureido)-5-phenoxysulfonylaniline (formula II)

48 g of 2-(3-acetylureido)-5-phenoxysulfonylnitrobenzene in 300 ml of methanol and 300 ml of 2-methoxyethanol are hydrogenated under normal pressure with a catalytic amount of Raney nickel. After hydrogen uptake is complete, the catalyst is filtered off with suction, washed with dimethylformamide and the solution is evaporated under reduced pressure. The residue is stirred with hot methanol, and the solid is filtered off cold under suction and washed with methanol and diisopropyl ether, melting point 202° C., decomposition.

EXAMPLE 8

Process (a)

1-Methoxycarbonyl-3-[5-(3-trifluoromethylphenylsulfonyloxy)-2-ureidophenyl]thiourea (formula I)

12 ml of methoxycarbonyl isothiocyanate are added dropwise, with stirring, to 18.7 g of 5-(3-trifluoromethylphenylsulfonyloxy)-2-ureidoaniline in 300 ml of dioxane, the temperature rising to about 40° C. The mixture is stirred for a further four hours without cooling, 60 ml of diisopropyl ether are added and the precipitate is filtered off with suction. After washing with diisopropyl ether, recrystallization is carried out from methanol/diisopropyl ether with the addition of active charcoal, melting point 190° C., decomposition.

EXAMPLE 9

Process (b)

N,N'-Bismethoxycarbonyl-N''-[5-(3-trifluoromethylphenylsulfonyloxy)-2-ureidophenyl]guanidine (formula I)

12.5 g of 5-(3-trifluoromethylphenylsulfonyloxy)-2-ureidoaniline, 13.6 g of N,N'-bismethoxycarbonyl-S-methylisothiourea and 100 mg of p-toluenesulfonic acid in 90 ml of ethyl acetate and 45 ml of methanol are stirred under reflux for 20 minutes. After cooling down, the mixture is evaporated to dryness under reduced pressure, and the residue is stirred with diisopropyl ether and filtered off with suction. Recrystallization from ethyl acetate/diisopropyl ether, melting point 131° C.

EXAMPLE 10

Process (b)

N-[2-(3-Acetylureido)-5-(3-trifluoromethylphenylsulfonyloxy)phenyl]-N',N''-bismethoxycarbonylguanidine (formula I)

14.6 g of 2-(3-acetylureido)-5-(3-trifluoromethylphenylsulfonyloxy)aniline, 12.4 g of N,N'-bismethoxycarbonyl-S-methylisothiourea and 75 mg of p-toluenesulfonic acid are stirred under reflux for two hours. After cooling down, the mixture is evaporated under reduced pressure, the residue is recrystallized from isopropanol and the crystals are stirred with cold ethyl acetate, filtered off with suction and washed, melting point 189° C., decomposition.

EXAMPLE 11

5-(3-Trifluoromethylphenylsulfonyloxy)-2-ureidoaniline (formula II)

61.5 g of 5-(3-trifluoromethylphenylsulfonyloxy)-2-ureidonitrobenzene in 200 ml of methanol and 200 ml of 2-methoxyethanol are hydrogenated under normal pressure with a catalytic amount of Raney nickel. After hydrogen uptake is complete, the catalyst is filtered off with suction, washed with methanol and the solution is evaporated under reduced pressure, 1 liter of water is added, and the solid is filtered off with suction, washed with water and dried over NaOH, melting point 172° C., decomposition.

EXAMPLE 12

5-(3-Trifluoromethylphenylsulfonyloxy)-2-ureidonitrobenzene (formula V)

30 ml of N-chlorosulfonyl isocyanate are added dropwise, at +10° C., to 108 g of 2-amino-5-(3-trifluoromethylphenylsulfonyloxy)nitrobenzene in 800 ml of toluene. The mixture is stirred for a further two hours while cooling, and 500 ml of petroleum ether are added. The 2-(3-chlorosulfonylureido)-5-(3-trifluoromethylphenylsulfonyloxy)nitrobenzene produced is filtered off with suction, washed with petroleum ether and dried over potassium hydroxide, melting point 137° C., decomposition. 150 g of this sulfochloride are introduced, with stirring and cooling in ice, into 2 liters of 1N HCl. The mixture is stirred for 2 hours while cooling and for 5 hours at room temperature, and next day the precipitate is filtered off with suction, washed with water to neutrality and dried, melting point 152° C.

EXAMPLE 13

2-(3-Acetylureido)-5-(3-trifluoromethylphenylsulfonyloxy)nitrobenzene (formula V)

1 ml of concentrated sulfuric acid is added, with stirring, to 60 g of 5-(3-trifluoromethylphenylsulfonyloxy)-2-ureidonitrobenzene in 200 ml of acetic anhydride. A clear solution is initially produced, and the temperature rises to about 40° C. The mixture is stirred for a further four hours, and the precipitate produced is filtered off with suction and washed with diisopropyl ether and petroleum ether, melting point 196° C.

EXAMPLE 14

2-(3-Acetylureido)-5-(3-trifluoromethylphenylsulfonyloxy)-aniline (formula II)

59 g of 2-(3-acetylureido)-5-(3-trifluoromethylphenylsulfonyloxy)nitrobenzene in 200 ml of methanol and 200 ml of 2-methoxyethanol are hydrogenated under normal pressure with a catalytic amount of Raney nickel. After hydrogen uptake is complete, the catalyst is filtered off with suction, washed with warm 2-methoxyethanol and the solution is evaporated under reduced pressure. Water is added to the residue and it is then filtered off with suction, washed with water and dried over sodium hydroxide, melting point 182° C.

In analogy to Examples 1–3, the following compounds of the formula I according to the invention, in which X denotes —O—SO$_2$— and R$^1$ denotes methyl (=formula Ia), are prepared:

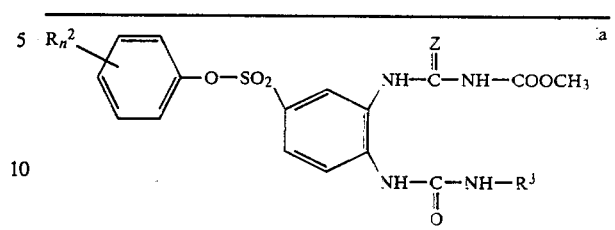

| Example | R$_n^2$ | R$^3$ | Z | Melting point [°C.] (D = Decomposition) |
|---|---|---|---|---|
| 15 | H | COCH$_3$ | N—COOCH$_3$ | 180 (D) |
| 16 | 4-CH$_3$ | H | S | 198 (D) |
| 17 | 4-CH$_3$ | H | N—COOCH$_3$ | 186 (D) |
| 18 | 4-CH$_3$ | COCH$_3$ | S | 215 (D) |
| 19 | 4-CH$_3$ | COCH$_3$ | N—COOCH$_3$ | 213 (D) |
| 20 | 4-C$_2$H$_5$ | H | S | 150 (D) |
| 21 | 4-C$_2$H$_5$ | COCH$_3$ | S | 205 (D) |
| 22 | 4-C$_2$H$_5$ | COCH$_3$ | N—COOCH$_3$ | 201 (D) |
| 23 | 4-i-C$_3$H$_7$ | H | S | 180 (D) |
| 24 | 4-i-C$_3$H$_7$ | H | N—COOCH$_3$ | 184 (D) |
| 25 | 4-i-C$_3$H$_7$ | COCH$_3$ | S | 210 (D) |
| 26 | 4-i-C$_3$H$_7$ | COCH$_3$ | N—COOCH$_3$ | 198 (D) |
| 27 | 4-s-C$_4$H$_9$ | H | S | 145 |
| 28 | 4-s-C$_4$H$_9$ | H | N—COOCH$_3$ | 186 (D) |
| 29 | 4-s-C$_4$H$_9$ | COCH$_3$ | S | 193 (D) |
| 30 | 4-t-C$_4$H$_9$ | H | S | 154 (D) |
| 31 | 4-t-C$_4$H$_9$ | H | N—COOCH$_3$ | 178 (D) |
| 32 | 4-t-C$_4$H$_9$ | COCH$_3$ | S | 225 (D) |
| 33 | 4-t-C$_4$H$_9$ | COCH$_3$ | N—COOCH$_3$ | 208 (D) |
| 34 | 3-CF$_3$ | H | S | 190 (D) |
| 35 | 3-CF$_3$ | H | N—COOCH$_3$ | 177 (D) |
| 36 | 3-CF$_3$ | CH$_3$CO | S | 230 |
| 37 | 3-CF$_3$ | CH$_3$CO | N—COOCH$_3$ | 190 |
| 38 | 2,4-Cl$_2$ | H | S | 160 |
| 39 | 2,4-Cl$_2$ | H | N—COOCH$_3$ | 183 |
| 40 | 2,4-Cl$_2$ | CH$_3$CO | S | 225 |
| 41 | 2,4-Cl$_2$ | CH$_3$CO | N—COOCH$_3$ | 189 |
| 42 | 2,3-Cl$_2$ | H | S | 195 |
| 43 | 4-C$_6$H$_5$ | H | S | 120 |
| 44 | 2-C$_6$H$_{11}$ | H | S | 201 |
| 45 | 2-C$_6$H$_{11}$, 4-CH$_3$ | H | S | 200 |
| 46 | 4-C$_6$H$_{11}$ | H | S | 205 |
| 47 | 4-F | H | S | 151 |
| 48 | 4-F | H | N—COOCH$_3$ | 180 |
| 48a | 3-F | H | S | 170 |
| 48b | 3-F | H | N—COOCH$_3$ | 180 |
| 48c | 2-F | H | S | 165 |
| 48d | 2-F | H | N—COOCH$_3$ | 180 |

The starting products of the formula II, in which X represents —O—SO$_2$— (=formula IIa), for Examples 15–48 are prepared in analogy to Examples 4–7 from the appropriate nitroamino compounds of the formula VIIa via the nitroureido compounds Va (X in formula V and VII=—O—SO$_2$—):

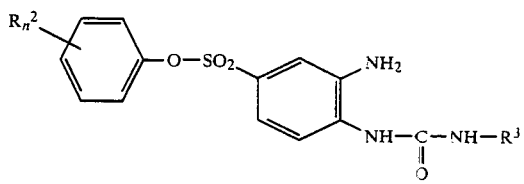

| | | Compound of the formula | | | Compound of the formula |
|---|---|---|---|---|---|
| Example | R$_n^2$ | VIIa, m.p. [°C.] | Va, m.p. [°C.] | R$^3$ | IIa, m.p. [°C.] |
| 49 | H | 97 | 190 | H | 180 (D) |
| 50 | H | | 198 | CH$_3$CO | 202 (D) |

-continued

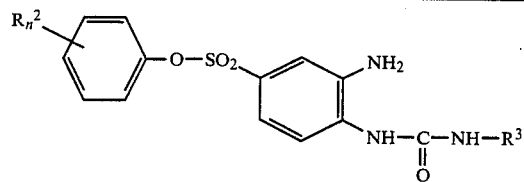

IIa

| Example | $R_n^2$ | Compound of the formula VIIa, m.p. [°C.] | Va, m.p. [°C.] | $R^3$ | Compound of the formula IIa, m.p. [°C.] |
|---|---|---|---|---|---|
| 51 | 4-CH$_3$ | 137 | 172 | H | 184 (D) |
| 52 | 4-CH$_3$ | | 215 | CH$_3$CO | 195 |
| 53 | 4-C$_2$H$_5$ | 98 | 175 | H | 178 (D) |
| 54 | 4-C$_2$H$_5$ | | 173 | CH$_3$CO | 160 |
| 55 | 4-i-C$_3$H$_7$ | 94 | 192 | H | 184 (D) |
| 56 | 4-i-C$_3$H$_7$ | | 199 | CH$_3$CO | 190 |
| 57 | 4-s-C$_4$H$_9$ | 100 | 135 | H | 170 (D) |
| 58 | 4-s-C$_4$H$_9$ | | 186 | CH$_3$CO | 160 (D) |
| 59 | 4-t-C$_4$H$_9$ | 148 | 198 | H | 172 (D) |
| 60 | 4-t-C$_4$H$_9$ | | 214 | CH$_3$CO | 198 |
| 61 | 3-CF$_3$ | 130 | 198 | H | 161 (D) |
| 62 | 3-CF$_3$ | | 183 | CH$_3$CO | 203 |
| 63 | 2,4-Cl$_2$ | 155 | 167 | H | 165 (D) |
| 64 | 2,4-Cl$_2$ | | 192 | CH$_3$CO | 185 |
| 65 | 2,3-Cl$_2$ | 176 | 218 | H | 172 (D) |
| 66 | 4-C$_6$H$_5$ | 152 | 188 | H | — |
| 67 | 2-C$_6$H$_{11}$ | Oil | 168 | H | 143 (D) |
| 68 | 2-C$_6$H$_{11}$, 4-CH$_3$ | Oil | 129 | H | Resin |
| 69 | 4-C$_6$H$_{11}$ | 120 | — | H | 270 (D) |
| 70 | 4-F | 110 | — | H | 154 (D) |
| 70a | 3-F | 116 | 171 | H | 254 (D) |
| 70b | 2-F | 125 | 120 | H | 278 (D) |

In analogy to Examples 8-10, the following compounds of the formula I according to the invention, in which
in which X denotes —SO$_2$—O— and
$R^1$ denotes methyl (=formula Ib),
are prepared, for example:

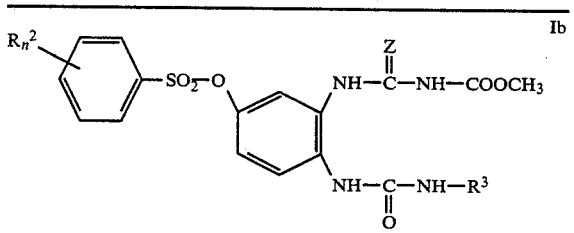

Ib

| Example | $R_n^2$ | $R^3$ | Z | m.p. [°C.] |
|---|---|---|---|---|
| 71 | H | H | S | 00 (D) |
| 72 | H | H | N—COOCH$_3$ | 190 (D) |
| 73 | 4-CH$_3$ | H | S | 180 (D) |
| 74 | 4-CH$_3$ | H | N—COOCH$_3$ | 192 (D) |
| 75 | 4-CH$_3$ | CH$_3$CO | S | 205 (D) |
| 76 | 4-CH$_3$ | CH$_3$CO | N—COOCH$_3$ | 194 |
| 77 | 4-C$_2$H$_5$ | H | S | 140 (D) |
| 78 | 4-C$_2$H$_5$ | H | N—COOCH$_3$ | 176 (D) |
| 79 | 4-C$_2$H$_5$ | CH$_3$CO | S | 205 (D) |
| 80 | 4-C$_2$H$_5$ | CH$_3$CO | N—COOCH$_3$ | 173 (D) |
| 81 | 4-i-C$_3$H$_7$ | H | S | 165 (D) |
| 82 | 4-i-C$_3$H$_7$ | H | N—COOCH$_3$ | 188 (D) |
| 83 | 4-i-C$_3$H$_7$ | CH$_3$CO | S | 222 (D) |
| 84 | 4-i-C$_3$H$_7$ | CH$_3$CO | N—COOCH$_3$ | 194 (D) |
| 85 | 4-s-C$_4$H$_9$ | H | S | 140 |
| 86 | 4-s-C$_4$H$_9$ | H | N—COOCH$_3$ | 151 (D) |
| 87 | 4-s-C$_4$H$_9$ | CH$_3$CO | S | 215 (D) |
| 88 | 4-s-C$_4$H$_9$ | CH$_3$CO | N—COOCH$_3$ | 175 (D) |
| 89 | 4-t-C$_4$H$_9$ | H | S | 170 (D) |
| 90 | 4-t-C$_4$H$_9$ | H | N—COOCH$_3$ | 150 (D) |
| 91 | 4-t-C$_4$H$_9$ | CH$_3$CO | S | 228 (D) |
| 92 | 4-t-C$_4$H$_9$ | CH$_3$CO | N—COOCH$_3$ | 202 |
| 93 | 3-CF$_3$ | CH$_3$CO | S | 220 (D) |

-continued

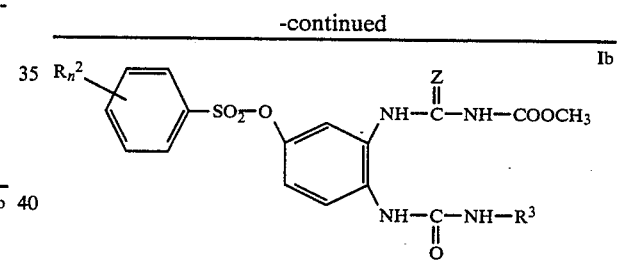

Ib

| Example | $R_n^2$ | $R^3$ | Z | m.p. [°C.] |
|---|---|---|---|---|
| 94 | 4-Cl | H | S | 188 (D) |
| 95 | 4-Cl | H | N—COOCH$_3$ | 198 (D) |
| 96 | 4-Cl | CH$_3$CO | S | 223 (D) |
| 97 | 4-Cl | CH$_3$CO | N—COOCH$_3$ | 145 (D) |
| 98 | 2-CF$_3$ | H | S | 173 (D) |
| 99 | 2-CF$_3$ | H | N—COOCH$_3$ | 186 (D) |
| 100 | 3,5-(CF$_3$)$_2$ | H | S | 191 (D) |
| 101 | 3,5-(CF$_3$)$_2$ | H | N—COOCH$_3$ | 182 (D) |
| 102 | 3,5-(CF$_3$)$_2$ | CH$_3$CO | S | 210 (D) |
| 103 | 3-CHF$_2$CF$_2$O | H | S | 147 (D) |
| 104 | 3-CHF$_2$CF$_2$O | H | N—COOCH$_3$ | 170 (D) |
| 105 | 4-F | H | S | 193 (D) |
| 106 | 4-F | H | N—COOCH$_3$ | 178 (D) |
| 107 | 4-Br | H | S | 186 (D) |
| 108 | 4-Br | H | N—COOCH$_3$ | 184 (D) |
| 109 | 2,5-Cl$_2$ | H | S | 179 (D) |
| 110 | 2,5-Cl$_2$ | H | N—COOCH$_3$ | 182 (D) |
| 111 | 4-OCH$_3$ | H | S | 120 |
| 112 | 4-OCH$_3$ | H | N—COOCH$_3$ | |
| 113 | 3-CH$_3$CO | H | S | 176 (D) |
| 114 | 3-CH$_3$CO | H | N—COOCH$_3$ | 168 (D) |
| 115 | 2,4,6-(i-C$_3$H$_7$)$_3$ | H | S | 191 (D0 |
| 116 | 2,4,6-(i-C$_3$H$_7$)$_3$ | H | N—COOCH$_3$ | |
| 116a | 3,5-(CF$_3$)$_2$ | CH$_3$CO | N—COOCH$_3$ | 195 (D) |
| 116b | 3-CH$_3$SO$_2$ | H | N—COOCH$_3$ | 142 (D) |
| 116c | 4-CH$_3$SO$_2$ | H | N—COOCH$_3$ | 190 (D) |

The starting products of the formula II, in which X represents —SO$_2$—O— (=formula IIb), for Examples 71-116 are prepared in analogy to Examples 11-14 from the appropriate nitroamino compounds of the formula VII b via the nitroureido compounds Vb (X in formula V and VII=—SO₂—O—):

alkyl moiety, or phenyl which is optionally substituted by halogen, methyl or methoxy,
X denotes —SO₂—O— or —O—SO₂— and
Z denotes =S; =N—COOR¹ or =NH.

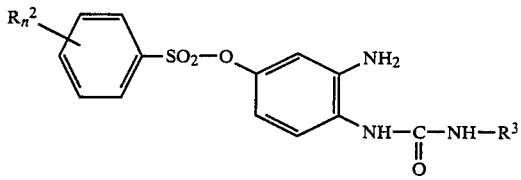

IIb

| Example | $R_n^2$ | Compound of the formula VIIb, m.p. [°C.] | Vb, m.p. [°C.] | $R^3$ | Compound of the formula IIb, m.p. [°C.] |
|---|---|---|---|---|---|
| 117 | H | 149 | 181 | H | 154 (D) |
| 118 | H | | — | CH₃CO | |
| 119 | 4-CH₃ | 155 | 180 | H | 162 (D) |
| 120 | 4-CH₃ | | 179 | CH₃CO | 195 |
| 121 | 4-C₂H₅ | 120 | 160 | H | 170 (D) |
| 122 | 4-C₂H₅ | | 185 | CH₃CO | 160 |
| 123 | 4-i-C₃H₇ | 105 | 160 | H | 150 (D) |
| 124 | 4-i-C₃H₇ | | 218 | CH₃CO | 182 (D) |
| 125 | 4-s-C₄H₉ | 70-72 | 112 | H | 145 (D) |
| 126 | 4-s-C₄H₉ | | 195 | CH₃CO | 165 (D) |
| 127 | 4-t-C₄H₉ | 125 | 153 | H | 173 (D) |
| 128 | 4-t-C₄H₉ | | 235 (Z) | CH₃CO | 203 (D) |
| 129 | 3-CF₃ | 132 | 152 | H | 172 (D) |
| 130 | 3-CF₃ | | 196 | CH₃CO | 182 |
| 131 | 4-Cl | 147 | 177 | H | 166 (D) |
| 132 | 4-Cl | | 188 | CH₃CO | 189 (D) |
| 133 | 2-CF₃ | 132 | 162 (Z) | H | — |
| 134 | 3,5-(CF₃)₂ | 154 | 194 | H | 171 (D) |
| 135 | 3,5-(CF₃)₂ | | 153 | CH₃CO | 201 (D) |
| 136 | 3-CHF₂CF₂O | Resin | Resin | H | — |
| 137 | 4-F | 161 | 178 | H | 158 (D) |
| 138 | 4-F | . | 185 | CH₃CO | — |
| 139 | 4-Br | 165 | 172 | H | 170 (D) |
| 140 | 2,5-Cl₂ | 189 | 182 | H | — |
| 141 | 4-OCH₃ | 102 | 178 (Z) | H | Resin |
| 142 | 3-CH₃CO | 142 | — | H | 162 |
| 143 | 2,4,6-(i-C₃H₇)₃ | 152 | 145 (Z) | H | — |
| 143a | 3-CH₃SO₂ | 148 | 148 (Z) | H | 180 (D) |
| 143b | 4-CH₃SO₂ | 181 | 190 (Z) | H | 280 (D) |

We claim:
1. A benzenesulfonic ester of the formula I

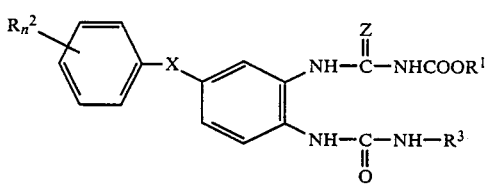

I in which
R¹ denotes straight-chain or branched alkyl having 1-4 carbon atoms, n denotes 1, 2 or 3 and the individual substituents R², independently of one another, denote hydrogen, fluorine, chlorine, bromine, iodine, cyano, nitro, trifluoromethyl, 1,1,2,2-tetrafluoroethoxy, straight-chain or branched alkyl having 1-12 carbon atoms, cycloalkyl having 3-8 carbon atoms, alkoxy, alkylthio, alkylsulfinyl or alkylsulfonyl, each having 1-6 carbon atoms in the alkyl radical, acetyl, acetamino, or phenyl, phenoxy, phenylthio, phenylsulfinyl or phenylsulfonyl, each of which is optionally substituted once or twice by halogen, R³ denotes hydrogen or —CO—R⁴, in which R⁴ denotes alkyl or alkoxyalkyl which are optionally substituted by halogen, and each of which have 1-6 carbon atoms in an 2. A compound according to formula I in claim 1, in which
R¹ denotes methyl and
R² denotes hydrogen, fluorine, chlorine, bromine, iodine, trifluoromethyl, 1,1,2,2-tetrafluoroethoxy, straight-chain or branched alkyl having 1-6 carbon atoms or cycloalkyl having 3-6 carbon atoms, and in which
R³ denotes hydrogen or —COR⁴,
in which
R⁴ denotes alkyl or alkoxyalkyl, each having 1-4 carbon atoms in an alkyl moiety, or phenyl.
X denotes —SO₂—O— or —O—SO₂— and
Z denotes =S or =NCOOCH₃ and
n denotes 1 or 2.
3. Pharmaceutical preparation for combatting helminths containing as the active ingredient an effective amount of a substituted benzenesulfonic ester of the formula I in claim 1, in admixture or conjunction with a customary pharmaceutical vehicle or mixed with a customary feedstuff.
4. Method of combatting helminths by administering to the patient a sufficient amount of a substituted benzenesulfonic ester of the formula I in claim 1.
5. N,N'-Bismethoxycarbonyl-N''-[5-(3-trifluoromethylphenylsulfonyloxy)-2-ureidophenyl]guanidine.

* * * * *